United States Patent [19]

Downs

[11] Patent Number: 4,571,082
[45] Date of Patent: Feb. 18, 1986

[54] APPARATUS AND METHOD FOR MEASURING REFRACTIVE INDEX

[76] Inventor: Michael J. Downs, 'Karibu', Furze Hill Rd., Headley Down, Hampshire, England

[21] Appl. No.: 495,431

[22] Filed: May 17, 1983

[30] Foreign Application Priority Data

May 18, 1982 [GB] United Kingdom ............... 8214383

[51] Int. Cl.$^4$ ............................................ G01N 21/45
[52] U.S. Cl. ..................................... 356/351; 356/361
[58] Field of Search ............................... 356/351, 361

[56] References Cited

U.S. PATENT DOCUMENTS 3,601,490  8/1971  Erickson .
3,625,616  12/1971  Lee ..................................... 356/361

OTHER PUBLICATIONS

Namba, "Photoelectric Recording Interferometer for Gas Analysis", *Rev. Sci. Instrum.*, vol. 30, No. 8, pp. 642–645, 8/59.
Hariharan et al., "Three-Beam Interferometer for Diffusion Measurements", *J. Sci. Instrum.*, vol. 39, pp. 165–167, 4/62.

*Primary Examiner*—Davis L. Willis
*Assistant Examiner*—Matthew W. Koren
*Attorney, Agent, or Firm*—Cushman, Darby & Cushman

[57] ABSTRACT

An interference refractometer of the Jamin type includes a beam splitter (14) arranged to split light from a laser source (12) into two partial beams $B_M$, $B_R$ one of which passes through a test cell (20) adapted to contain a fluid medium. One component ($B_R$) of the reference partial beam passes through a phase plate which introduces a 90 degree phase shift. The partial beams are detected by photodetectors (38, 44, 46) the outputs of which are coupled to counter circuits (not shown) to provide an output which is independent of changes in the mean level of the optical input signals.

8 Claims, 3 Drawing Figures

APPARATUS AND METHOD FOR MEASURING REFRACTIVE INDEX

This invention relates to a device for measuring the absolute refractive index of a gas or a liquid, for comparing the refractive indices of two gases or two liquids, or for measuring changes in the refractive index of a solid.

A major application of a refractometer is to measure the absolute refractive index of the ambient atmosphere so that a length-measuring interferometric system which has a path length in air can be compensated for changes in temperature, pressure and humidity.

The basic principle of an interference refractometer has been known for over a century, and was investigated by Jamin in 1856 and by Rayleigh in 1896. Modern interference refractometers still use an identical optical arrangement of a double pass enclosure containing a gas under test, with a prism reflector to provide a return beam displaced from the input beam, but still passing through the test enclosure. A refrence beam travelling outside the enclosure is also reflected by the prism. The difference between the optical path length of the measuring beam in the presence and absence of a test gas is determined by counting the interference fringes as the test gas is pumped out of the enclosure.

A Jamin-type instrument provides one interferogram, which can be regarded as an a.c. signal, corresponding to the interference fringes, superimposed on a mean d.c. level. The magnitude of the d.c. level depends on variations in the alignment and the relative sizes of the interfering beams, attenuation in one or both of the beams, and on intensity fluctuations of the light source. Such variations are not fully predictable.

A modern automatic reversible fringe counting circuit for use with an interferometric system requires either a stable mean d.c. level so that a trigger level can be set, or preferably a signal having a constant mean d.c. level of zero volts; a Jamin-type interferometer with its changing d.c. level does not conform to this requirement. It is an object of the present invention to provide an interference refractometer which can be used with a conventional reversible fringe-counting system which generates from the optical outputs of the interferometer two electrical counting signals varying sinusoidally with path difference and in phase quadrature. Each signal has a constant mean d.c. level of zero volts even when the light intensity and contrast are varying in the interferometer.

According to the invention, there is provided an interference refractometer comprising beam splitting means arranged to divide an incident beam of electromagnetic radiation into first and second spaced parallel partial beams having components of substantially equal intensity in two orthogonal directions of radiation, reflection means spaced from the beam splitting means and arranged to reflect said first partial beam along its path to said reflection means and said second partial beam along a parallel path, a test device positioned between the beam splitting means and the reflection means so that said first partial beam will traverse a path of known length therein, phase shifting means arranged to introduce a phase shift of substantially 90 degrees between radiation polarised in two orthogonal directions in one of the two partial beams, a polarising beam splitter arranged to receive from the beam splitting means radiation having components of substantially equal intensity derived from the first and second partial beams, first and second radiation sensing means each arranged to receive from the polarising beam splitter radiation polarised at one of said two orthogonal directions, third radiating sensing means arranged to receive from the beam splitting means radiation derived only from the second partial beam and signal subtraction means for extracting a signal derived from the third sensing means from each of the first and second sensing means.

Usually the two alternating output signals will be supplied to a conventional fringe-counting circuit.

Preferably the beam splitting means is a Jamin type beam splitter prism comprising a rectangular parallel-sided block of optically transparent material having a fully-reflecting face and an opposite partly-reflecting face. The beam splitter can be arranged to divide an incident beam into parallel partial beams and to divide and combine the partial beams reflected by the reflection means to give the required two output beams. The reflection means is preferably a focusing lens having a plane mirror at its focus, the first partial beam travelling along the optical axis of the lens and being normally incident on the mirror.

The test device may comprise an elongated enclosure with optically transparent end walls, the enclosure being connectable to a vacuum pump or to a supply of gas or liquid. In a variation the elongated enclosure is surrounded by a second enclosure through which the second partial beam travels before and after reflection, the second enclosure also being connectable to a vacuum pump or to a supply of gas or liquid. The test device may also comprise support means arranged to support an optically transparent solid so that the first partial beam passes twice through the solid.

Also according to the invention, there is provided a method of sensing change in refractive index comprising providing first and second partial beams of electromagnetic radiation having equal amplitudes in two orthogonal directions of polarisation, causing the first partial beam to traverse a transparent medium along an optical path of known length reflecting said partial beam so that it traverses said path through said medium in the reverse direction, causing the second partial beam to traverse a path of equal length but not passing through said medium, introducing a phase difference of 90 degrees between radiation in two orthogonal directions of polarisation in one of the partial beams, combining components of equal intensity derived from the first and second partial beams to provide first and second output signals deriving a third output signal corresponding to the intensity of the second partial beam only, subtracting the third output signal from each of the first and second output signals and causing a change in the optical path length of the first partial beam through said medium.

The invention will now be described by way of example only with reference to the accompanying drawing in which:

FIG. 3 is a longitudinal and a transverse section of a second form of a test cell for use in the refractometer.

Figure 1:
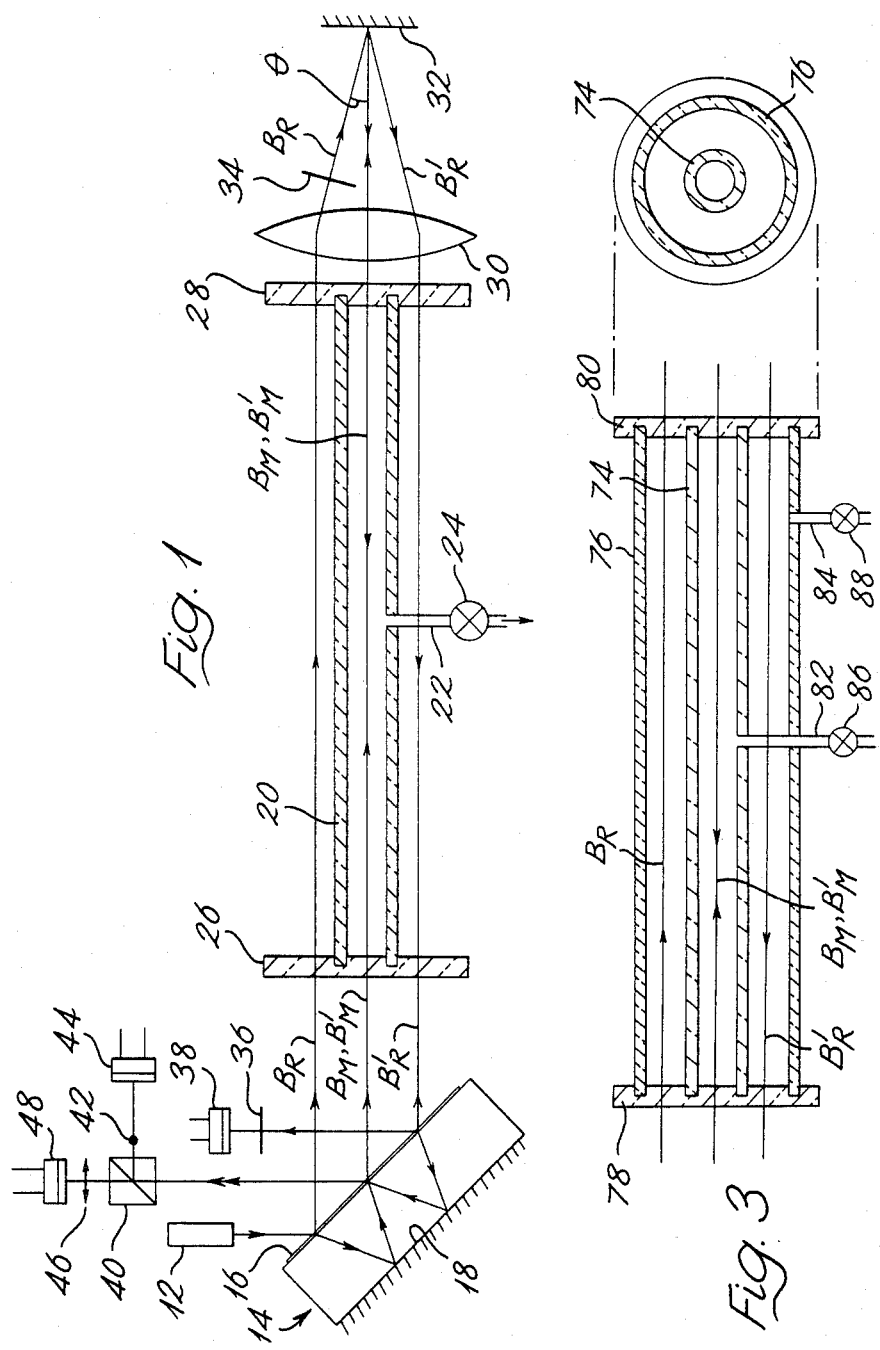
FIG. 1 is a schematic illustration of the optical components of an interference refractometer according to the invention.

In FIG. 1 a plane polarised beam from a laser 12 is incident at 45° on a Jamin type beam splitter prism 14 which is a parallel-sided glass block having a semi-reflecting front surface 16 and a fully-reflecting rear surface 18. The front surface 16 transmits part of the incident beam which is reflected by the rear surface 18 to provide a first partial beam, the measuring beam $B_M$. The front surface reflects the other part of the incident beam to provide a second partial beam, the reference beam $B_R$. The measuring and reference beams are parallel.

Adjacent to the beam splitter is an elongated enclosure 20, conveniently a glass tube, which can be evacuated or connected to the atmosphere or a gas supply through a connecting pipe 22 and valve 24. The enclosure has first and second end walls 26, 28 transverse to its long axis. The end walls are optically transparent, parallel, and parallel sided, and they are of considerably greater diameter than the enclosure 20.

The enclosure 20 and its end walls 26 are positioned so that the measuring beam $B_M$ passes through the first end wall 26 into the enclosure 20, while the reference beam $B_R$ passes through the first end wall 26 but travels outside the enclosure parallel to the measuring beam. The measuring beam $B_M$ leaves the enclosure through the second end wall 28, and the reference beam also passes through the second end wall.

Adjacent the second end wall 28 is a focusing lens 30 and at the lens focus is a plane mirror 32 perpendicular to the axis of the enclosure 20. The measuring beam $B_M$ passes through the centre of the lens 30, is incident normally on the mirror 32, and is reflected as a beam $B'_M$ to retrace its path through the enclosure to the beam splitter 18.

The reference beam $B_R$, which is displaced from the lens axis, is deviated by the lens 30 so as to be incident on the mirror at a small angle of incidence $\theta$, and at a position coincident with the focus of the lens, the reflected beam $B'_R$ passing again through the lens which deviates it to travel parallel to the input beam $B_R$ but on the opposite side of the enclosure 20. There is a phase plate 34 between the lens 30 and the mirror 32. The reflected reference beam $B'_R$ passes through the second and first end walls 28, 26, to the beam splitter 14.

At the prism 14, a part of the reflected reference beam $B'_R$ is reflected by the front surface 16 through a polariser 36 to a first photodetector 38. The remainder of the beam $B'_R$ is transmitted by the front surface 16 and reflected by the rear surface 18 to a polarising beam splitter 40 which also receives the reflected measuring beam $B'_M$ after reflection by the front surface 16. The polarising beam splitter 40 reflects a beam at a first direction of polarisation through an aligned polariser 42 to a second photodetector 44, and transmits a beam at the orthogonal direction of polarisation through an aligned polariser 46 to a third photodetector 48.

Inspection of FIG. 1 shows that, of the two beams received by the polarising beam splitter 40, each beam has undergone at the beam splitter 14 one relfection by the front surface 16, and two transmissions through the front surface 16, so that if the respective intensity losses on reflection and transmission are R and T, both beams have been attenuated by the same factor $RT^2$. Further, both means have passed twice through each end wall 26, 28, and twice through the lens 30. The optical path lengths are therefore equal, provided the enclosure 20 contains air at the same ambient temperature, pressure and humidity as the air through which the refracted beam has passed. If the enclosure is then evacuated, the optical path length of the measuring beam $B_M$ will alter, and interference fringes will occur. If the number of fringes is counted during the evacuation, and the internal length of the enclosure 20 is known, the refractive index of the air initially contained in it can be readily calculated.

In the arrangement illustrated in FIG. 1, the input and reflected measuring beams $B_M$, $B_M'$, are superimposed. This commonpath optical arrangement has the usual advantage of insensitivity to tilt or alignment errors in the apparatus or to vibration and a small-diameter enclosure 20 can be used. There is a further advantage arising from the use of the lens and plane mirror. As the beams are reflected, the wavefronts are doubly inverted, i.e. inverted in both planes. The second passage of the measuring beam through the enclosure 20 therefore compensates for any inhomogeneities; for example, if the enclosure 20 contains a turbulent liquid, the effect of the turbulence is eliminated. The presence of any tilt fringes introduced by optical components is also eliminated.

In the prior art arrangement in which the input and reflected measuring beams are spatially separated in the enclosure 20, tilt fringe effects would be doubled in the second passage of the beam and the contrast in the interferometer could be completely eliminated. Operation with a turbulent liquid would be impossible.

In the refractometer according to the invention, the measuring and the reference beams both contain equal components at each of two orthogonal directions of polarisation P and S. The polarising beam splitter therefore receives four input components, a P and S component from each of the measuring and the reference beams.

The beam splitter 40 separates the components at different polarisations. The photodetectors 44, 48 receive radiation only at one direction of polarisation, but having equal contributions originating in the measuring $B_M$ and the reference $B_R$ beams; the beams therefore interfere if there is an optical path difference between the beam $B_M$ and $B_R$ and produce fringes, either set of these fringes could be counted as the enclosure 20 is evacuated to give an identical result, but both signals have a mean d.c. level which is not zero volts at this stage. The two signals are however in phase quadrature as a result of the phase plate 34.

The phase plate 34 between the lens 30 and the mirror 32 introduces a phase retardation into one polarisation component of the reference beam $B_R$ such that the interference fringes at this direction of polarisation are in phase quadrature with light polarised in the orthogonal direction.

It is a major feature of an interferometer according to the invention that a signal is provided which is responsive to all the variations to which the two interfering beams are subject, but which does not contain interference information. This signal is provided by the first photodetector 38. Light incident on it is derived only from the reference beam $B_R$, i.e. this signal is responsive only to variations proportional to the mean d.c. level of the two interfering light beams, and the d.c. signal from the photodetector 38 can be used as a compensation signal by subtraction from the signals from the photodetectors 44, 48. The compensated signals then comprise two a.c. signals in phase quadrature with a mean d.c. level of zero volts. The signals can be supplied to a conventional reversible fringe counting system; the trigger levels of these signals are automatically conpensated against variations in contrast and light source intensity. Use of such a system has not previously been possible with a Jamin-type interference refractometer.

Figure 2:
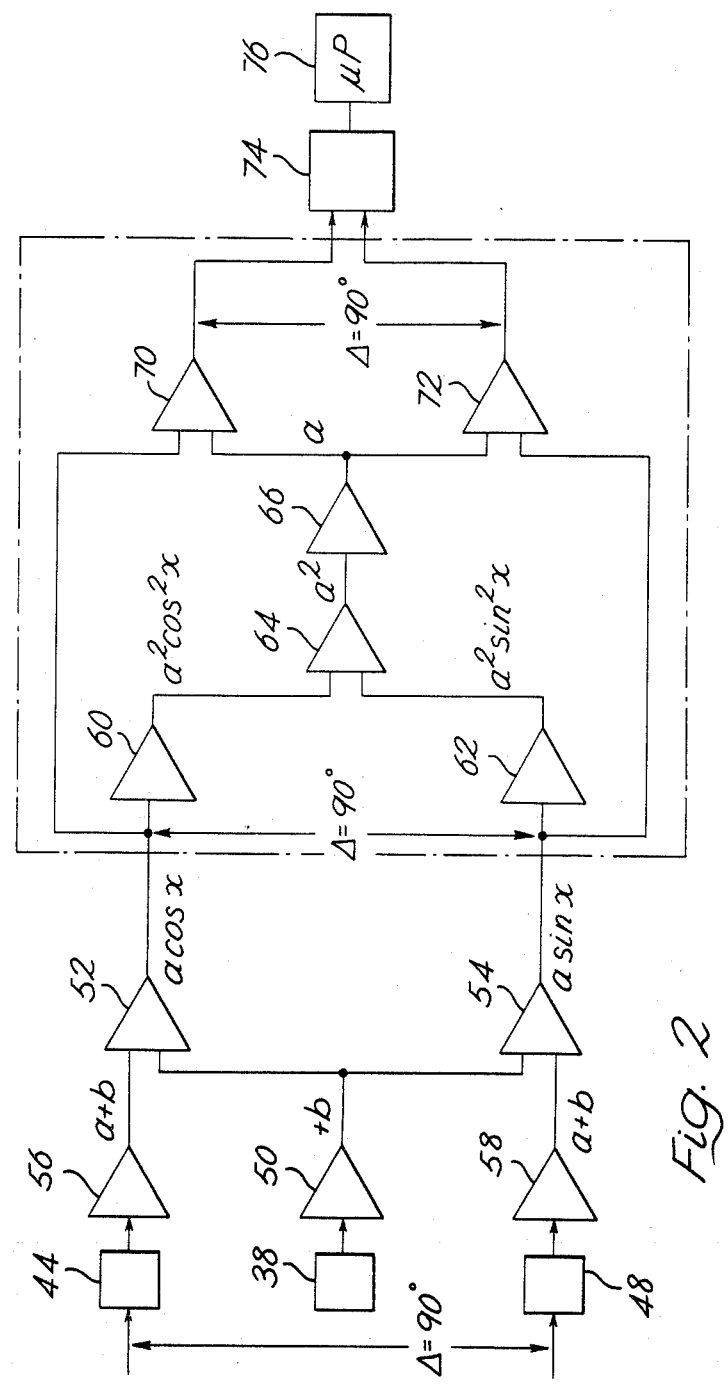
FIG. 2 is an illustration of the electronic components of an interference refractometer according to the invention.

Referring now to FIG. 2, the first photodetector 38 is connected through an amplifier 50 to one input of each of two different amplifiers 52, 54. The second and third photodetectors 44, 48, are connected through amplifiers 56, 58 respectively to the other input of each difference amplifier.

As explained above the inputs to the photodetectors 44, 48 are in phase quadrature, indicated as $=90°$ in FIG. 2. The inputs can be regarded as having an a.c. component a due to the interference between the partial beams, superimposed on a mean d.c. level b. The input to the photodetector 38 has no a.c. component and is equal only to the d.c. component b. The difference amplifiers 52, 54 subtract the d.c. component and provide output signals having only a sinusoidally varying component, the signals still being in phase quadrature. They can be regarded as sine or cosine signals of maximum amplitude a, i.e. a sin x and a cos x.

The output signals from the amplifiers 52, 54 are therefore suitable for direct connection to a conventional fringe counting system, but may advantageously be further modified by passage through the optional AGC (automatic gain control) system indicated within the dotted lines in FIG. 2. The AGC system comprises two squarers 60, 62, connected through a summing amplifier 64 to a square root circuit 66 which supplies a signal to one input of each of two ratio amplifiers 70, 72. The outputs from the difference amplifiers 52, 54 are connected to the respective squarers 60, 62 and also to the other input of the respective ratio amplifiers 70, 72.

The squarers 60, 62 provide signals corresponding to $a^2 \sin^2 x$ and $a^2 \cos^2 x$, which are summed then square rooted to give an output signal of amplitude a; the ratio amplifiers 70, 72 derive the a.c. frequency from the signals connected directly from the difference amplifiers 52, 54 and provide phase quadrature signals of equal, constant amplitude for connection to an automatic fringe counter 74.

Either with or without the optional AGC circuit, the phase quadrature signals supplied to a conventional fringe counting circuit 74 allow a fringe count from which the change in path length in the enclosure can be calculated and, when the length of the enclosure 20 is known, related by known formulae to the refractive index of the air initially contained within the enclosure.

Referring now to both FIG. 1 and FIG. 2, the method of use of the refractometer is as follows. The valve 24 is opened to allow the enclosure to equilibrate with the atmosphere. The gains of the amplifiers 52 and 54 and 56 are equalised, and the outputs of amplifier 52 and 54 are equalised by rotating the direction of polarisation of the input beam, i.e. rotating the laser. This gives equal components in orthogonal polarisation directions in the measuring and reference beams. The polariser 36 is then rotated to attenuate the beam incident on the photodetector 38 while viewing one interferogram on an oscilloscope, and the polariser rotated until the a.c. signal is symmetrical about the 0 volt rail, i.e. the mean d.c. level is zero volts. The phase quadrature outputs, either from the difference amplifiers 52, 54, or from the ratio amplifiers 70, 72 when present, are connected to the fringe counter 74 which is zeroed. The enclosure 20 is then evacuated and the fringes counted as the optical path length changes. The refractive index of the gas initially in the enclosure 20 can be calculated from the fringe count by a microprocessor 76 if required.

It is to be noted that a differential measurement is made. The apparatus is set to one condition, and the fringe count corresponding to a slow change in conditions is measured.

The refractive index of a gas other than the atmosphere can be measured, so that either the pressure of a known gas, or the concentration of a component of a gas mixture at known pressure can be determined. Similarly, changes in the refractive index of a liquid can be monitored.

The double inversion applied to incident wavefronts by the plane mirror 32 allows the system to be operated with a liquid in the enclosure 20; if thermal turbulence is present, or if the liquid is optically active or is a polarising liquid, the double inversion causes cancellation of the effects during the second passage of the measuring beam. Usually the device will be used to monitor the concentration of a solution by calibrating the device and then providing successive samples to the enclosure 20 for measurement.

A differential measurement can also be made if a small change in optical path difference is expected. The single enclosure illustrated in FIG. 1 will be replaced by the double enclosure illustrated in FIG. 3. A central circular enclosure 74 is surrounded by a second enclosure 76. Both enclosures are closed by plane, transparent end walls 78, 80, and the enclosures are separately evacuatable or connected to the atmosphere or a gas supply by respective connecting pipes 82, 84 and valves 86, 88.

The double enclosure is positioned so that the measuring beam $B_M$ passes through the central enclosure before and after reflection and the reference beam $B_R$ travels through the second enclosure before and after reflection as illustrated. The gas mixture to be tested is supplied to the central enclosure 74 and a known reference gas, which may be the ambient atmosphere, admitted to the second enclosure 76. The fringe counter is then zeroed. The two gases are then slowly exchanged until the second enclosure contains the test gas mixture and the first enclosure contains the reference gas and the counter is re-zeroed. From the fringe count, the refractive index of the test gas, and therefore the concentration of a known component, can be calculated. The double cell is advantageously used when a small change in refractive index is to be measured, or to compare two gases or two liquids.

The fact that in both the single and the double enclosure arrangement a differential measurement is made does not allow measurement of the absolute refractive index of a solid, but refractive index changes of an optically transparent solid can be sensed by zeroing the fringe counter with the solid in the position normally occupied by the enclosure 20. Any subsequent fringe count will correspond to a change in index.

In an interference refractometer ccording to the invention, high accuracy and high sensitivity are achievable. With a helium-neon laser and an enclosure 31.64 centimeters long, an absolute accuracy of 2.5 parts in $10^7$ has been obtained directly from the fringe counting signals, additional fringe sub-division allowing even higher accuracy. The system sensitivity is of the order 1 part in $10^9$, and it is stable to about 2.5 parts in $10^9$.

The common path interferometer system employed makes the device insensitive to alignment errors or to inaccurately parallel or parallel-sided end walls. The enclosure 20 can be located in V-block supports so that it is easily removable and replaceable, and high quality end walls are not needed. An unstabilised laser can be provided. Although the reference beam is not in a common path arrangement, it passes through the same components as the measuring beam, so that its path length changes with ambient temperature in the same way as that of the measuring beam, and it is reflected by the same plane mirror.

One possible source of small errors is that thermal expansion may vary the distance between the lens 30 and the plane mirror 32. The error is a cosine function of the angle of incidence $\theta$ of the reference beam $B_R$, i.e. the angle at the mirror between the measuring and reference beams. $\theta$ is typically about 10° or 15° so that the system is insensitive to length changes; a change in the spacing of 75 to 100 times the fringe spacing is needed to generate one spurious fringe.

In a variation of the use of the device, the density of the fluid in the test enclosure can be measured. The subtraction of the d.c. signal level does not compensate for a difference in density in the fluids through which the measuring and reference beams pass, but the square root of the sum of the $\cos^2$ and $\sin^2$ signals is proportional to the d.c. component in both beams, and the usual d.c. signal from the photodetector 38 gives the d.c. component in the reference beam, so the d.c. component in the measuring beam, which is proportional to the density of a fluid under test, can be derived and the density calculated.

While the invention has been described as having a single frequency input from a laser source, it is also capable of operating with a multiple frequency or a white light source.

I claim:

1. An interference refractometer comprising beam splitting means arranged to divide an incident beam of electromagnetic radiation into first and second spaced parallel partial beams having components of substantially equal intensity in two orthogonal directions of radiation, reflection means spaced from the beam splitting means and arranged to reflect said first partial beam along its path to said reflection means and said second partial beam along a parallel path, a test device positioned between the beam splitting means and the reflection means so that said first partial beam will traverse a path of known length therein, phase shifting means arranged to introduce a phase shift of substantially 90 degrees between radiation polarised in two orthogonal directions in one of the two partial beams, a polarising beam splitter arranged to receive from the beam splitting means radiation having components of substantially equal intensity derived from the first and second partial beams, first and second radiation sensing means each arranged to receive from the polarising beam splitter radiation polarised at one of said two orthogonal directions, third radiating sensing means arranged to receive from the beam splitting means radiation derived only from the second partial beam and signal subtraction means for extracting a signal derived from the third sensing means from each of the first and second sensing means.

2. An interference refractometer as claimed in claim 1 further comprising counter means connected to said third sensing means.

3. An interference refractometer as claimed in claim 1 including a beam splitter prism comprising a substantially rectangular parallel-side block of optically transparent material having a fully-reflecting face opposite a partially-reflecting face.

4. An interference refractometer as claimed in claim 3 wherein said reflection means comprises a converging lens having a plane mirror at its focus and positioned with its axis along the path of said first partial beam.

5. An interference refractometer as claimed in claim 1 including a test device comprising an elongated enclosure with transparent end walls and being adapted for connection to evacuating means and to fluid supply means.

6. An interference refractometer as claimed in claim 5 wherein said elongated enclosure is surrounded by a second enclosure also being adapted for connection to evacuating means and to fluid supply means.

7. An interference refractometer as claimed in claim 1 including support means arranged to support an optically transparent solid object in the path of said first partial beam.

8. A method of sensing change in refractive index comprising providing first and second partial beams of electromagnetic radiation having equal amplitudes in two orthogonal directions of polarisation, causing the first partial beam to traverse a transparent medium along an optical path of known length reflecting said partial beam so that it traverses said path through said medium in the reverse direction, causing the second partial beam to traverse a path of equal length but not passing through said medium, introducing a phase difference of 90 degrees between radiation in two orthogonal directions of polarisation in one of the partial beams, combining components of equal intensity derived from the first and second partial beams to provide first and second output signals deriving a third output signal corresponding to the intensity of the second partial beam only, subtracting the third output signal from each of the first and second output signals and causing a change in the optical path length of the first partial beam through said medium.

* * * * *